United States Patent
Doyle et al.

(10) Patent No.: US 10,390,531 B2
(45) Date of Patent: Aug. 27, 2019

(54) MATERIALS INCORPORATING LIGHT ACTUATED FLUOROAZOBENZENES

(71) Applicant: International Business Machines Corporation, Armonk, NY (US)

(72) Inventors: Matthew S. Doyle, Chatfield, MN (US); Jeffrey N. Judd, Oronoco, MN (US); Joseph Kuczynski, North Port, FL (US); Scott D. Strand, Rochester, MN (US); Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 64 days.

(21) Appl. No.: 15/588,287

(22) Filed: May 5, 2017

(65) Prior Publication Data

US 2018/0317479 A1    Nov. 8, 2018

(51) Int. Cl.
| | |
|---|---|
| *A01N 33/26* | (2006.01) |
| *D03D 25/00* | (2006.01) |
| *A01N 25/10* | (2006.01) |
| *D03D 1/00* | (2006.01) |
| *D03D 15/00* | (2006.01) |

(52) U.S. Cl.
CPC .......... *A01N 33/26* (2013.01); *D03D 1/0035* (2013.01); *D03D 15/00* (2013.01)

(58) Field of Classification Search
None
See application file for complete search history.

(56) References Cited

U.S. PATENT DOCUMENTS

| | | | | |
|---|---|---|---|---|
| 4,043,999 A | * | 8/1977 | Model | C09B 43/11 534/599 |
| 2004/0173115 A1 | * | 9/2004 | Crabtree | D06P 1/5271 101/483 |

FOREIGN PATENT DOCUMENTS

| | | |
|---|---|---|
| CN | 105040126A A | 11/2015 |
| CN | 105286104 A | 2/2016 |
| CN | 105648750 A | 6/2016 |

OTHER PUBLICATIONS

Machine translation of CN105040126, Kumar et al. (Year: 2015).*
Kumar et al., "A Chaotic Self-Oscillating Sunlight-Driven Polymer Actuator," Nature Communications, Received Mar. 4, 2016, Accepted May 19, 2016, Published Jul. 4, 2016. pp. 1-8.

* cited by examiner

*Primary Examiner* — Shawn Mckinnon
(74) *Attorney, Agent, or Firm* — Patterson + Sheridan, LLP

(57) ABSTRACT

Embodiments of the disclosure generally provide compositions and methods involving textiles that repel insects by vibrations and oscillations. The random and chaotic oscillations are caused by molecular bond isomerizations in the textile material driven by visible light, such as sunlight.

20 Claims, 6 Drawing Sheets

R = Organic Group

US 10,390,531 B2

MATERIALS INCORPORATING LIGHT ACTUATED FLUOROAZOBENZENES

FIELD

The present disclosure generally relates to textiles that repel insects by vibratory oscillations.

BACKGROUND

Arthropod pests such as flies, mosquitoes, and ticks are responsible for disease and loss of life among humans and other animals, and incur financial losses associated with loss of work productivity due to illness and health care costs. Among the increasing number of arthropod-borne diseases, only a few are preventable by vaccines. For example, there is no effective vaccine against malaria, and the only way to avoid the disease is avoidance of a mosquito bite, which is difficult to achieve in environments where mosquitos thrive. For this reason, the first lines of defense for humans includes the use of bite-blocking fabrics (e.g., tightly woven clothing and netting) and/or the application of chemical repellents to a fabric and/or skin.

New functional textiles with insect repellency have been developed for use in clothing, netting, and tents, and typically consist of a textile that is coated with an insect repellent chemical compound, such as a pyrethrin and/or pyrethroid. These compounds have low-toxicity profiles towards humans, and effectively control a variety of insect pests. Despite these favorable characteristics, the utility of the pyrethrins and pyrethroids in textiles is limited because of their relatively short-lived insecticidal action. This is due to the poor washing fastness of repellent textile finishing formulas and the decomposition of the compounds into non-active, non-insecticidal products in the presence of oxygen and ultraviolet light. Therefore, it would be an advantage to have an insect repellant functional textile, fabric or cloth that maintains insect repellant properties despite multiple wash cycles, abrasion, and/or exposure to ultraviolet light or oxygen, and that does not use a chemical insecticide that exudes a repellant vapor.

CLAIM SUMMARY

Described herein is an insect repellant textile with a plurality of woven fibers that contain fluoroazobenzene groups which vibrate when exposed to visible light, such as blue light and green light, and/or sunlight with wavelengths of light from 400 nm to 700 nm.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of the disclosure and are therefore not to be considered limiting of its scope, for the disclosure may admit to other equally effective embodiments.

DETAILED DESCRIPTION

The present disclosure provides compositions and methods involving insect repellant textiles, fabrics and cloth. In embodiments of this disclosure, new functional textiles are described that exhibit chaotic oscillations and/or vibrations that prevent or otherwise repel an insect from holding fast onto a textile material. The vibrations in the fabric therefore may annoy the insect so that it does not choose to remain on the fabric, and/or the insect may be detached or flicked off before the insect can bite a human host.

Figure 1:
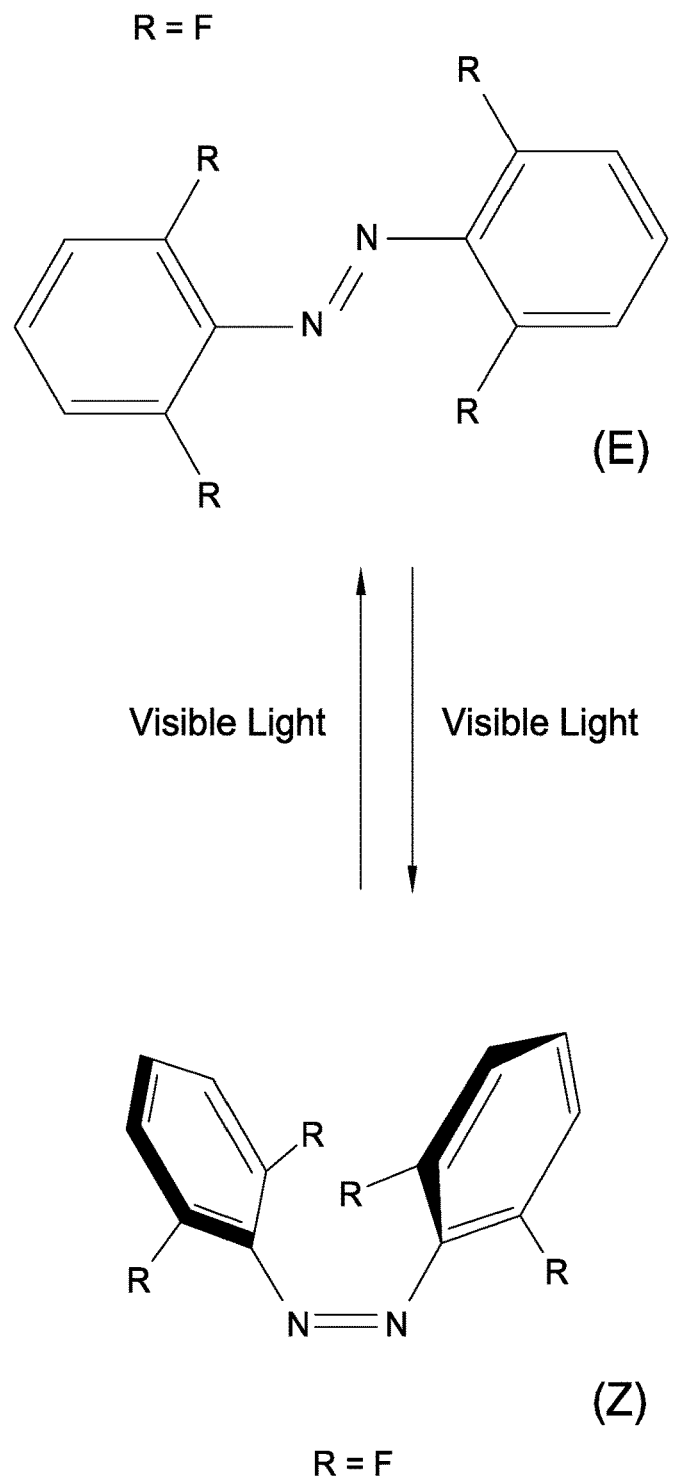
FIG. 1 illustrates molecular bonding changes according to some embodiments of this disclosure.

The vibratory motions or oscillations in the insect repellent fabric according to embodiments of this disclosure are a result of a reversible molecular bond isomerization(s) that are caused by visible light absorption. The rapid and reversible bond isomerizations produce oscillations that may detach, flick-off, annoy, and harass insects, so that the insects cannot hold fast to a textile surface. As shown in FIG. 1, where R=fluorine, the textiles of this disclosure contain fluoroazobenzene (F-azo) compounds or groups that undergo both trans→cis (E→Z) and cis→trans (Z→E) isomerizations when exposed to visible light and/or sunlight, thus producing oscillations and vibrations in the material. For example, in one embodiment, a textile comprising F-azo groups may undergo a trans→cis (E→Z) isomerization at wavelengths at or about 400 nm, and cis→trans (Z→E) isomerization at or about 500 nm wavelengths or longer. We note that the cis or Z conformation is the high energy state conformation, and thus requires a higher energy or shorter wavelength of light to cause or activate a trans→cis (E→Z) isomerization. Conversely, a trans or E state of an F-azo molecule or group is a lower energy conformation, and a cis→trans (Z→E) isomerization may be activated by a lower energy or longer wavelength of light. As illustrated by FIG. 1, a strong electron withdrawing group (EWG), such as fluorine, ortho to the azo group, adjusts the energy of the molecular orbitals such that both trans→cis (E→Z) and cis→trans (Z→E) isomerizations may both occur when irradiated by light in the visible spectrum such as sunlight, due to an n→π* electronic excitation or transition. In embodiments of this disclosure, we do not restrict the aromatic ring position of the substitution (e.g., ortho, meta, or para with respect to the azo group), or the identity of the group that causes the visible light isomerizations.

Figure 2:
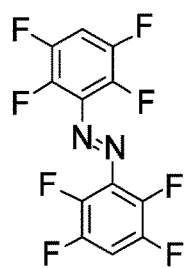
FIG. 2 illustrates some chemical structures according to some embodiments of this disclosure.
Figure 2:
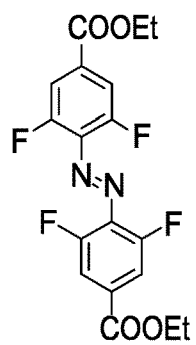
Figure 2:
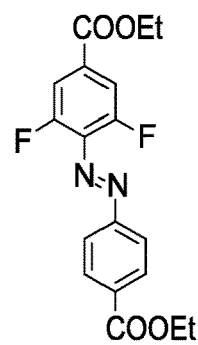
Figure 2:
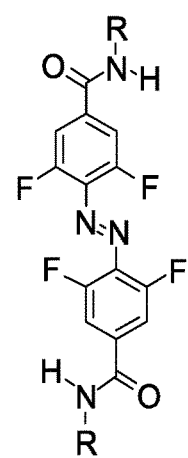
Figure 3:
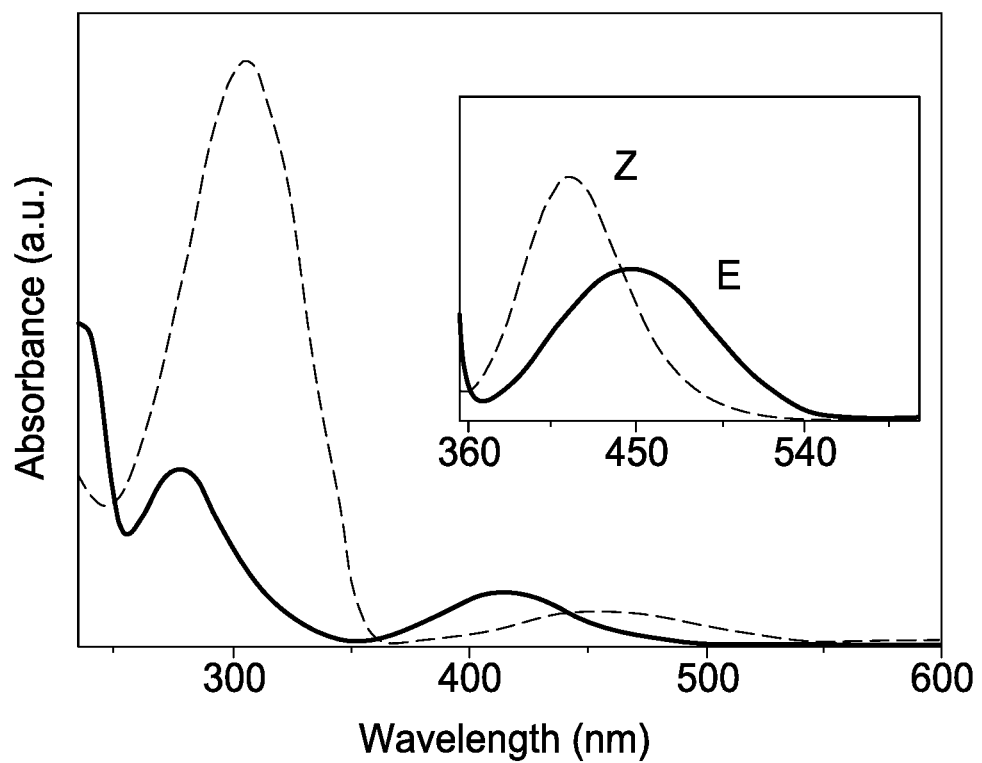
FIG. 3 illustrates absorption spectra according to some embodiments of this disclosure.

FIG. 3 shows ultraviolet-visible (UV-Vis) absorption spectra illustrating the absorptions that produce the trans→cis (E→Z) and cis→trans (Z→E) photoisomerization in some F-azo compounds. The inset figure is an expanded view of the visible absorptions that produce the photoisomerization in the visible light spectrum, and the associated bond conformations. FIG. 2 illustrates some F-azo compounds that may undergo this type of photoisomerization when exposed to visible light and/or sunlight, with various benzene ring substitutions, such as positional, symmetric, asymmetric, and functional groups that may undergo further chemical reactions, such as ester and amide. In summary, both trans→cis (E→Z) and cis→trans (Z→E) isomerizations in F-azo compounds may occur when irradiated with visible light, and create chaotic and reversible oscillations through a material such as a textile, fabric or cloth that contains the F-azo compounds. Those skilled in the art may choose the position and type of molecular and atomic group substitutions on the F-azo compounds of this disclosure to produce the desired absorption maxima for the two isomers. In this disclosure, we do not restrict the wavelengths of visible light that the F-azo compounds may absorb to cause, effect, or actuate the photoisomerization response.

Figure 4:
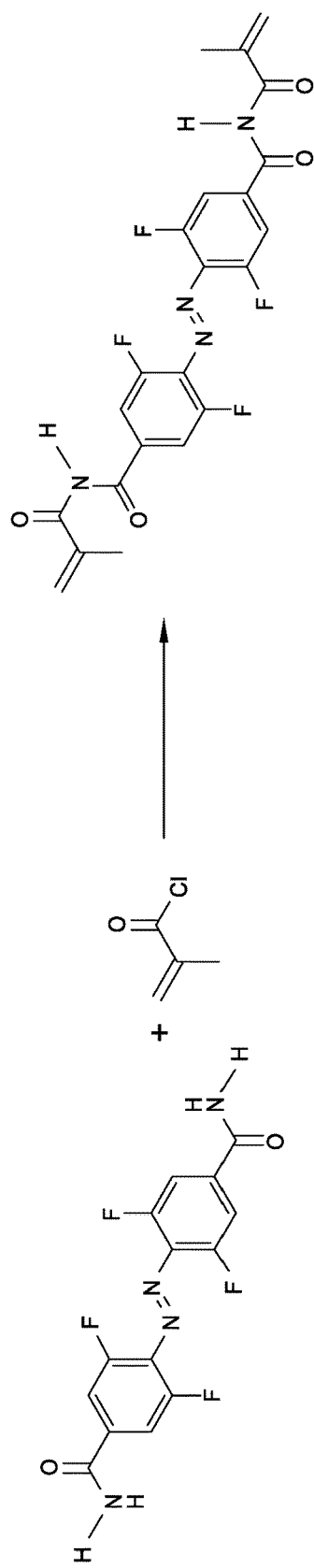
FIG. 4 illustrates a chemical reaction according to some embodiments of this disclosure.

In some embodiments, F-azo molecules, oligomers and polymers may have functional groups that may undergo chemical reactions that may produce fibers and textiles containing covalently bonded F-azo groups. Any type of fiber or textile may be used, such as (a) protein/animal sourced, (b) cellulosic/plant source, (c) modified cellulosic (e.g., synthetically modified cellulose) and, (d) pure synthetic fibers. Respective examples include, but are not restricted to: (a) wool, silk, mohair, and cashmere, (b) cotton and linen, (c) rayon, and (d), polyamides, polyesters, and acrylics. In one embodiment, F-azo groups may be covalently attached or grafted onto a textile fiber that has surface functional groups that will react with F-azo compound functional groups. In another example, functional F-azo molecules, oligomers and polymers that contain the appropriate chemical groups may copolymerize with textile fiber monomers, oligomers, or polymers to form a material containing F-azo groups in the polymer backbone (main chain) or that are attached at the main chain ends, or are pendant with respect to the main chain. In embodiments of this disclosure, an F-azo molecule with at least one unsaturated functional group (e.g., vinyl, acrylic) may be copolymerized with at least one unsaturated monomer, oligomer, or polymer, such as vinyl, allyl, or an acrylic monomer and/or oligomer, to produce a new synthetic acrylic textile. As shown in FIG. 4, an F-azo diacrylate may be produced by reacting methacryloyl chloride with a bi-functional amide F-azo compound, which may then be subsequently polymerized with any combination of acrylic monomers, oligomers, or polymers by a suitable method such as a free radical polymerization, initiated by heat, light, or oxidation/reduction (redox) couples. After polymerization, the acrylic polymer, containing F-azo groups, may be spun or drawn into textile fibers by any suitable method. Alternatively, an F-azo monoacrylate may be used, so that the F-azo group is a pendant group in relation to the main chain or backbone group. In one embodiment, an F-azo diacrylate, from the F-azo diamide, may be synthesized as follows: a round bottom flask containing a solution of NaH (240 mg) in anhydrous ethyl ether (10 mL) may be cooled to 0° C. under anhydrous conditions and blanketed with argon. To this magnetically stirred mixture, an F-azo diamide, neat or dissolved in a suitable dry solvent, may be added in a dropwise fashion (672 mg, 2 mmol) until gaseous bubbling subsides. After about 10 minutes of stirring, methacryloyl chloride (0.39 mL, 4 mmol) may be added dropwise, and the solution may be stirred between about 10 min to about 45 minutes. Work-up of the reaction mixture may then be achieved by slow dropwise addition of cold water, ether extraction of the organic phase, followed by drying of the organic phase over $MgSO_4$. The F-azo diacrylate may then be purified by column chromatography, and analyzed by a number of methods including nuclear magnetic resonance, ultraviolet-visible spectroscopy, and infrared spectroscopy. Preparation of an acrylic F-azo polymer from the corresponding F-azo diacrylate may be achieved as follows: a weight percent (wt %) mixture is prepared in a suitable dry and oxygen free vessel containing the following materials: F-azo diacrylate 10-15 wt %, Sartomer polyester acrylate oligomer CN2254 NS 60-70 wt %, and Sartomer polyester acrylate oligomer CN2262 10-20 wt %. The wt % of the F-azo compound may be empirically determined to maximize the oscillatory displacement, and may be at least 2 wt %. Polymerization of the mixture may be achieved by any method available to those skilled in the arts, including suspension, emulsion and solution polymerization techniques. Any suitable free radical initiator may be used with the above techniques, including inorganic compounds such as persulphate, chlorates or hydrogen peroxide. In one example, a redox catalyst system is used that contains ammonium or potassium persulphate (oxidizer), sodium bisulphate (reducing agent) and ferric or ferrous ion (catalyst). Spinning or production of acrylic fibers derived from the polymerization of the aforementioned mixture may be achieved by any method, and may include a process that involves solution/dope preparation, spinning, solvent removal, washing, drying, cutting and bailing.

Coating an F-azo polymer on a textile and/or a fiber may cause a useful vibratory response and repel insects. In an embodiment of this disclosure, a film or coating of an F-azo polymer on a fiber or textile may be produced by ultraviolet (UV) light photopolymerization. For example, the aforementioned acrylate mixture may include a suitable photoinitiator, such as IGM Resins Omnirad BEM photoinitiator (2-5 wt %), and the mixture may then be applied to a textile surface by blade or spray coating, or applied to a fiber upon or after fiber drawing. After application of the mixture, the surface of the textile or fiber may be exposed to a suitable UV light source, such as an LED light or a mercury bulb, to polymerize and cure the coating.

We do not restrict the type of reaction or the mechanism by which the F-azo compound or groups reacts to form a fiber or a textile containing F-azo groups. Reaction types used to produce polymers and textiles that contain F-azo groups may include, but are not restricted to: synthesis, decomposition, single replacement and double replacement, oxidation/reduction, acid/base, nucleophilic, electrophilic and radical substitutions, addition/elimination reactions, grafting and chain extension; and polymerization reactions such as condensation, step-growth, chain-growth and addition, acrylic free radical, cationic epoxy, Michael addition, ring-opening, and ring-forming or Diels-Alder polymerization types.

In an embodiment of this disclosure, a polyamide containing F-azo groups may be produced from a diamino F-azo compound and an acid chloride, to produce a nylon-like polyamide. Those skilled in the art may choose any solvent system to achieve dissolution of the reacting compounds, and/or use an interfacial or biphasic polymerization depending on the solubility of the components. In one example, a suitable vessel containing a 3 wt % sodium hydroxide solution and between about 2 mL to about 5 mL of an F-azo diamine is prepared. In a separate vessel, 1 mL to 3 mL of sebacyl chloride is dissolved in about 50 mL of hexane. The sebacyl chloride solution may be slowly and gently added to the F-azo diamine solution so as to form two layers. The F-azo amide polymer thus formed in the top layer may be isolated or fibers may be drawn from the interface of the two solutions. The polymer may also be vacuum dried overnight and then analyzed for structure, purity, and thermal properties by methods such as nuclear magnetic resonance, size exclusion chromatography, and differential scanning calorimetry. The F-azo containing polyamide may contain any sufficient number of F-azo groups, as determined empirically, so that a useful oscillatory response is achieved when exposed to visible light.

Figure 5:
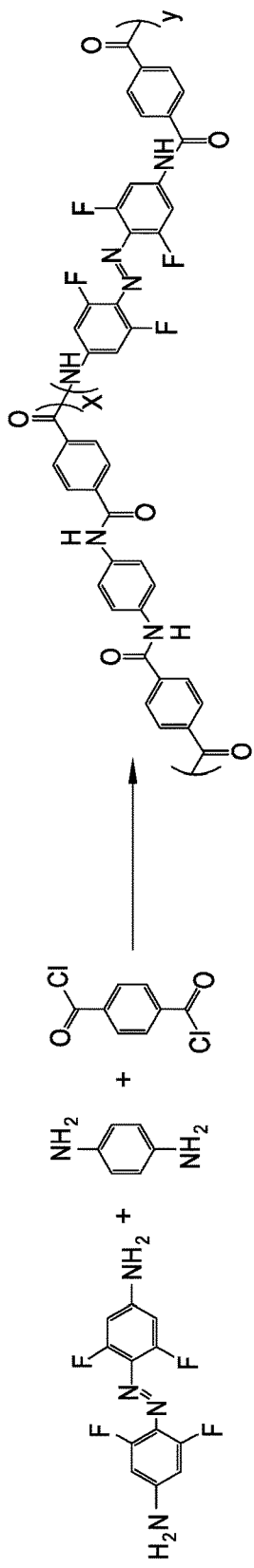
FIGS. 5(A) and 5(B) illustrates some chemical reactions according to some embodiments of this disclosure.
Figure 5:
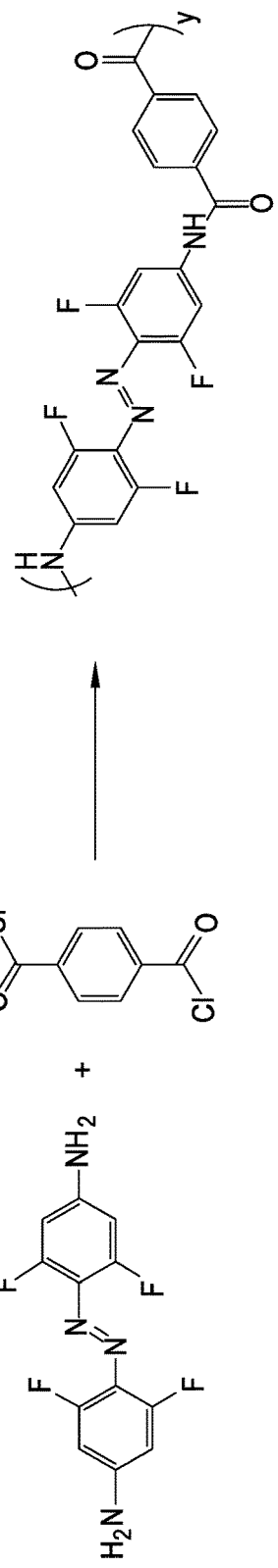

Polyamides containing F-azo groups with high aromatic content may be produced from an F-azo diamine and an aromatic diacyl (acid) chloride (e.g., terephthaloyl chloride) as illustrated by FIGS. 5(A) and 5(B), using a suitable solvent such as dimethylacetamide (DMA) or N-methyl-pyrrolidone (NMP) and calcium chloride. In the case of 5(A), the aromatic content is adjusted by addition of a non-F-azo diamine, and a copolymer may be formed depending on the relative reactivity of the diamine(s) to the diacyl chloride. In an example, as illustrated by FIG. 5(B), an F-azo polyamide may be prepared as follows: a dry and degassed round bottom flask, cooled in an ice bath, is charged with dry N-methyl-pyrrolidone (NMP) and calcium chloride containing 3% by weight triethyl amine, and 1 mmol of terephthaloyl chloride and a magnetic stir bar. To the magnetically stirred terephthaloyl chloride solution, an F-azo diamine (1.1 mmol) may be added dropwise over about 30 minutes. Depending on the temperature and solubility of the polymer thus formed, the F-azo polyamide may be isolated and purified, or the polymer solution may be used directly to draw fibers.

Figure 6:
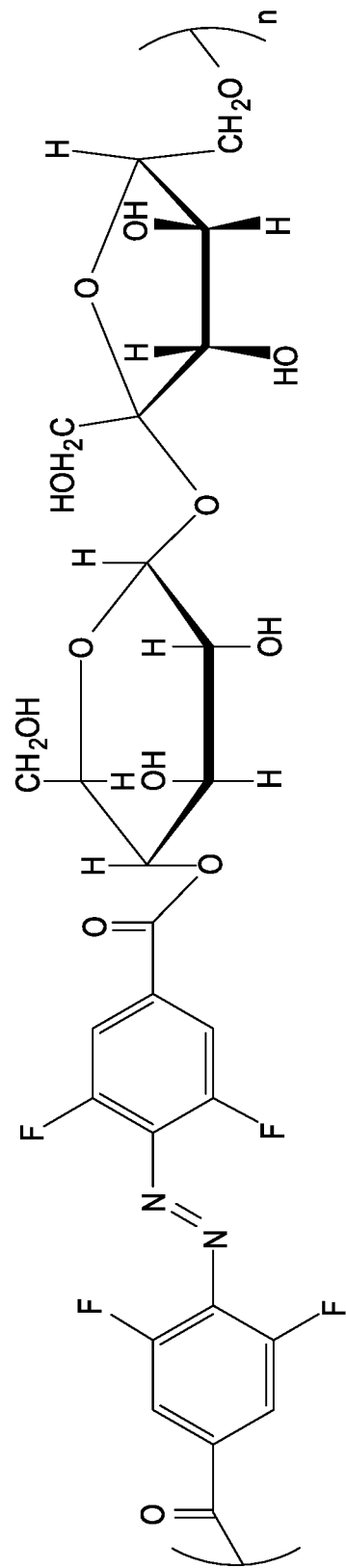
FIG. 6 illustrates a chemical structure according to some embodiments of this disclosure.

In other embodiments of this disclosure, a sugar or cellulose polymer containing F-azo groups may be prepared, as illustrated by a polymer structure containing F-azo groups and sucrose groups, as shown in FIG. 6. This polymer and related derivatives may be produced by any number of synthetic schemes, including but not restricted to esterification or transesterification reactions. In one example, an esterification reaction may occur by reacting one mole equivalent of an F-azo compound with two carboxylic acid groups at the para positions with one or more mole equivalents of a suitable sugar containing two primary alcohols, under esterification conditions (acid or base catalysis). Alternatively, an F-azo diester may undergo a transesterification reaction with a suitable sugar containing two primary alcohols under transesterification conditions (acid or base catalysis, heating and alcohol removal). Those skilled in the art may choose any suitable reaction conditions to produce polyesters containing F-azo groups, and the F-azo groups may be any group that will produce an ester group and/or linkage in the desired product. The compounds, reagents, and materials described herein may be obtained from any number of commercial sources including Sigma-Aldrich of St. Louis, Mo., USA.

Non-covalent bonding interactions involving F-azo compounds or groups and a fiber or a textile containing F-azo groups may also include ionic and hydrogen bonding interactions. In one embodiment, F-azo groups may also be attached to a fiber by non-covalent interactions, such as ionic interactions. For example, a fiber may have a plurality of surface positive charges, such as those produced by quaternary ammonium groups, and may be contacted with F-azo molecules, oligomers or polymers (in a solution or in emulsion) that have negatively charged groups, such as phosphate or sulfate groups, using a process such as padding, dip or spray coating, and thus produce a fiber with a surface coating of F-azo molecules, oligomers or polymers. In another embodiment, the fiber, such as a cellulosic fiber, may have hydrogen bonding groups (e.g., hydroxyl, carboxylic) that may bond with F-azo molecules, oligomers or polymers containing hydrogen bonding groups, and thus produce a fiber with a surface coating of F-azo molecules, oligomers or polymers. In further embodiments, a textile that contains F-azo groups may be a physical mixture of textile fibers, such as at least two fibers that are co-woven together. In one case, at least one of the fibers may contain F-azo groups, and the other co-woven fiber(s) may not contain F-azo groups. In the embodiments that include covalent, non-covalent, and physical blends or weaves, we note that the weight percent or mole fraction of F-azo groups must be sufficient so that the textile exhibits a useful oscillatory response when exposed to visible light and/or sunlight.

While the foregoing is directed to embodiments of the present disclosure, other and further embodiments of the disclosure may be devised without departing from the basic scope thereof, and the scope thereof is determined by the claims that follow.

What is claimed is:

1. An insect repellant textile, comprising:
a plurality of woven fibers, comprising fluoroazobenzene groups, which vibrate when exposed to visible light, wherein at least one of the fluoroazobenzene groups comprises one or more of the following moieties:

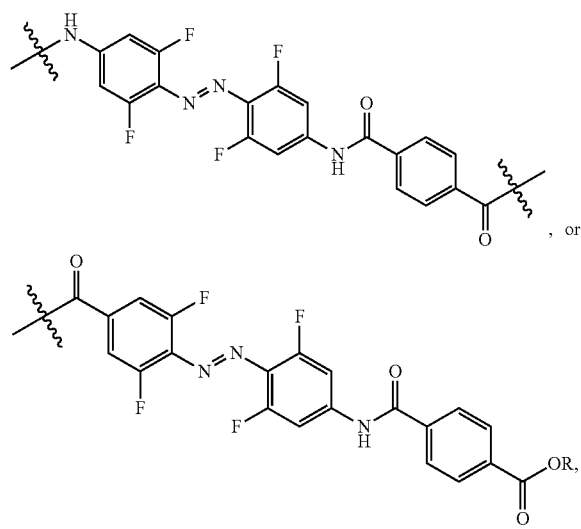

wherein the —OR group comprises a sugar.

2. The insect repellant textile of claim 1, wherein the plurality of woven fibers vibrates when exposed to sunlight.

3. The insect repellant textile of claim 2, wherein the plurality of woven fibers vibrate when exposed to light having a wavelength from 400 nm to 700 nm.

4. The insect repellant textile of claim 2, wherein the plurality of woven fibers vibrate when exposed to blue light and green light.

5. The insect repellant textile of claim 1, wherein one or more of the fluoroazobenzene groups are selected from the group consisting of ortho, meta, and para fluoroazobenzene groups.

6. The insect repellant textile of claim 5, wherein one or more of the fluoroazobenzene groups include ortho-fluoroazobenzene groups.

7. The insect repellant textile of claim 1, wherein the plurality of woven fibers include cis and trans bond isomerization reaction products.

8. The insect repellant textile of claim 1, wherein one or more of the fluoroazobenzene groups have an E molecular conformation.

9. The insect repellant textile of claim 1, wherein one or more of the fluoroazobenzene groups have a Z molecular conformation.

10. The insect repellant textile of claim 1, wherein the fluoroazobenzene groups have a mixture of E and Z molecular conformations.

11. The insect repellant textile of claim 1, wherein one or more of the fluoroazobenzene groups are covalently bonded to the plurality of woven fibers.

12. The insect repellant textile of claim 11, wherein one or more of the fluoroazobenzene groups are a reaction product of a copolymerization reaction.

13. The insect repellant textile of claim 1, wherein one or more of the fluoroazobenzene groups are bonded to the plurality of woven fibers by a bond type selected from the group consisting of ionic bonding and hydrogen bonding.

14. The insect repellant textile of claim 1, wherein the plurality of woven fibers comprise a natural fiber.

15. The insect repellant textile of claim 14, wherein the natural fiber is selected from the group consisting of protein containing fibers, cellulosic fibers, and synthetically modified cellulosic fibers.

16. The insect repellant textile of claim 1, wherein the plurality of woven fibers comprise a synthetic fiber.

17. The insect repellant textile of claim 16, wherein the synthetic fiber is made from a material selected from the group consisting of polyolefin, polyacrylic, polyester, and polyamide.

18. The insect repellant textile of claim 1, wherein the plurality of woven fibers comprises co-woven natural and synthetic fibers.

19. The insect repellant textile of claim 1, wherein the fluoroazobenzene groups are at least 2% by weight based on a textile weight.

20. An insect repellant textile, comprising:
a plurality of woven fibers, comprising fluoroazobenzene groups, which vibrate when exposed to visible light, wherein at least one of the fluoroazobenzene groups comprises one or more of the following moieties:

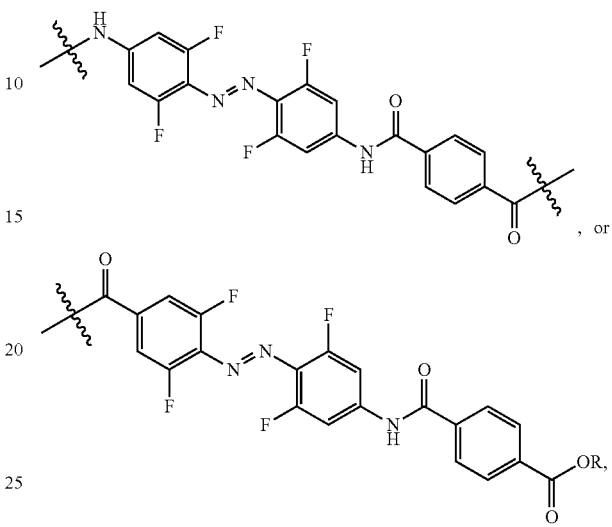

wherein the —OR group comprises a sugar, and wherein one or more of the fluoroazobenzene groups are covalently bonded to the plurality of woven fibers.

* * * * *